(12) United States Patent
Baura

(10) Patent No.: US 7,043,293 B1
(45) Date of Patent: May 9, 2006

(54) METHOD AND APPARATUS FOR WAVEFORM ASSESSMENT

(75) Inventor: Gail D. Baura, San Diego, CA (US)

(73) Assignee: CardioDynamics International Corporation, San Diego, CA (US)

( * ) Notice: Subject to any disclaimer, the term of this patent is extended or adjusted under 35 U.S.C. 154(b) by 340 days.

(21) Appl. No.: 10/329,129

(22) Filed: Dec. 24, 2002

(51) Int. Cl.
*A61B 5/0402* (2006.01)

(52) U.S. Cl. .................................................. 600/509

(58) Field of Classification Search ......... 600/508–521
See application file for complete search history.

(56) References Cited

U.S. PATENT DOCUMENTS

| | | | |
|---|---|---|---|
| 5,101,828 A | 4/1992 | Welkowitz et al. | |
| 5,309,917 A | 5/1994 | Wang et al. | |
| 5,390,679 A | 2/1995 | Martin | |
| 5,423,326 A | 6/1995 | Wang et al. | |
| 5,442,543 A | 8/1995 | Tresp | |
| 5,443,073 A | 8/1995 | Wang et al. | |
| 5,543,795 A | 8/1996 | Fernald | |
| 5,634,465 A * | 6/1997 | Schmiesing et al. | 600/454 |
| 5,685,316 A | 11/1997 | Schookin et al. | |
| 5,913,826 A | 6/1999 | Blank | |
| 5,999,845 A * | 12/1999 | dePinto | 600/509 |
| 6,007,491 A | 12/1999 | Ling et al. | |
| 6,016,445 A | 1/2000 | Baura | |
| 6,099,477 A | 8/2000 | Archibald et al. | |
| 6,161,038 A | 12/2000 | Schookin et al. | |
| 6,186,955 B1 | 2/2001 | Baura | |
| 6,249,595 B1 | 6/2001 | Foxall et al. | |
| 6,253,103 B1 | 6/2001 | Baura | |
| 6,281,681 B1 | 8/2001 | Cline et al. | |
| 6,292,689 B1 | 9/2001 | Wallace et al. | |
| 6,310,967 B1 | 10/2001 | Heine et al. | |
| 6,326,971 B1 | 12/2001 | Van Wieringen | |
| 6,561,986 B1 | 5/2003 | Baura et al. | |
| 6,602,201 B1 | 8/2003 | Hepp et al. | |
| 6,636,754 B1 | 10/2003 | Baura et al. | |

FOREIGN PATENT DOCUMENTS

WO    WO 02/079776    10/2002

OTHER PUBLICATIONS

Mathematical Programming Glossary by Harvey Greenberg, relevant pages only including cover pp. 1-2 and Glossary p. 7 of 10 (date unknown) (Copyright 1996-2003) (http://carbon.cudenver.edu).

(Continued)

*Primary Examiner*—Scott M. Getzow
(74) *Attorney, Agent, or Firm*—Gazdzinski & Associates

(57) ABSTRACT

An improved method and apparatus for assessing time-variant waveforms and identifying artifacts of interest therein. In one exemplary embodiment, an iterative interval search technique is applied to ECG waveform data in order to identify one or more artifacts (e.g., right atrial and right ventricular "spikes") within the waveform in conjunction with a fuzzy logic noise threshold analysis. This technique allows for robust artifact identification in waveforms where significant variations in noise and artifact periodicity may exist. The identified artifact(s) may then be used as an input to another process, such as being substituted as an ECG "Q" point for subsequent fiducial point detection within a cardiographic impedance waveform. Apparatus including computer programs for implementing the aforementioned techniques are also disclosed.

48 Claims, 9 Drawing Sheets

OTHER PUBLICATIONS

The Human Heartbeat web pages by The Golden Number from the Phi Nest (date unknown) (Copyright The Evolution of Truth, 1999-2003) (http://goldennumber.net/heartbeat.htm).

Mathtools.net web page re Fuzzy and Neural Approaches in Engineering by Leften H. Tsoukalas and Robert E. Uhrig (date unknown) (www.mathworks.com).

Neural Network Toolbox for Use with MATLAB—User's Guide Version 3.0, relevant pages only including cover page, contact page, p. vi, pp. 1-16 and 1-17.

* cited by examiner

METHOD AND APPARATUS FOR WAVEFORM ASSESSMENT

COPYRIGHT

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

This invention relates generally to the field of waveform analysis, and particularly in the exemplary embodiments to methods and apparatus for evaluating physiologic waveforms such as those present in the impedance cardiograms and electrocardiograms of a living subject.

2. Description of Related Technology

Time variant waveforms are commonplace in many technological disciplines. Analysis of such waveforms, including features or artifacts contained therein, can be useful for obtaining information regarding the waveform itself or the source of the waveform.

Waveform Analysis

A variety of techniques for waveform analysis are known under the prior art. One such technique is known as the "golden section search." The golden section search is part of a larger class of analysis techniques referred to herein as "iterative interval" methods. The golden section search is a method of locating a maximum or minimum in a quantity or bracket of data. This technique involves evaluating the function at some point x in the larger of the two intervals (a,b), or (b,c). For location of the maximum, if f(x)>f(b) then x replaces the midpoint b, and b becomes an end point. If f(x)<f(b), then b remains the midpoint with x replacing one of the end points. Either way the width of the bracketing interval will reduce and the position of the minima will be better defined. FIG. 1 illustrates this process graphically, where the initial bracket (1,2,3) becomes (4,2,3), (4,2,5), and so forth.

The foregoing procedure is then repeated until the width achieves a desired tolerance. It can be shown that if the new test point, x, is chosen to be a given proportion ("golden section") along the larger sub-interval, measured from the mid-point b, then the width of the full interval will reduce at an optimal rate. The golden section search advantageously requires no information about the derivative of the function itself. If such information is available it can be used to predict where best to choose the new point x in the above algorithm, leading to faster convergence.

Cardiovascular Analysis

One exemplary class of waveforms which are of significant interest are those generally relating to the cardiovascular function of living subjects. Included within this class of waveforms are electrocardiographs (ECGs) and impedance cardiographs (ICGs). As is well known, the study of the performance and properties of the cardiovascular system of a living subject has proven useful for diagnosing and assessing any number of conditions or diseases within that subject. The performance of the cardiovascular system, including the heart, has characteristically been measured in terms of several different parameters, including the stroke volume and cardiac output of the heart.

Noninvasive estimates of cardiac output (CO) can be obtained using the well known technique of impedance cardiography (ICG). Strictly speaking, impedance cardiography, also known as thoracic bioimpedance or impedance plethysmography, is used to calculate the stroke volume (SV) of the heart. As shown in Eqn. (1), when the stroke volume is multiplied by heart rate, cardiac output is obtained.

$$CO = SV \times \text{heart rate}. \quad \text{(Eqn. 1)}$$

During impedance cardiography, a constant alternating current, with a frequency such as 70 kHz, $I(t)$, is applied across the thorax. The resulting voltage, $V(t)$, is used to calculate impedance. Because the impedance is assumed to be purely resistive, the total impedance, $Z_T(t)$, is calculated by Ohm's Law. The total impedance consists generally of a constant base impedance, $Z_o$, and time-varying impedance, $Z_c(t)$, as shown in Eqn. 2:

$$Z_T(t) = \frac{V(t)}{I(t)} = Z_o + Z_c(t). \quad \text{(Eqn. 2)}$$

The time-varying impedance is believed to reflect the change in resistance of the blood as it transverses through the aorta.

Stroke volume is typically calculated from one of three well known equations, based on this impedance change:

$$\text{Kubicek: } SV = \rho\left(\frac{L^2}{Z_o^2}\right) LVET \frac{dZ(t)}{dt_{\max}}, \quad \text{(Eqn. 3)}$$

$$\text{Sramek: } SV = \frac{L^3}{4.25 Z_o} LVET \frac{dZ(t)}{dt_{\max}}, \quad \text{(Eqn. 4)}$$

$$\text{Sramek-Bernstein: } SV = \delta \frac{(0.17H)^3}{4.25 Z_o} LVET \frac{dZ(t)}{dt_{\max}}. \quad \text{(Eqn. 5)}$$

Where:
  L=distance between the inner electrodes in cm,
  LVET=ventricular ejection time in seconds,
  $Z_o$=base impedance in ohms, $\frac{dZ(t)}{dt_{\max}}$ = magnitude of the largest negative derivative of the impedance change,
  $Z_c(t)$, occuring during systole in ohms/s, $\rho$ = resistivity of blood in ohms-cm,
  $H$ = subject height in cm, and
  $\delta$ = special weight correction factor.

magnitude of the largest negative derivative of the impedance change, $Z_c(t)$, occurring during systole in ohms/s,
ρ=resistivity of blood in ohms-cm,
H=subject height in cm, and
δ=special weight correction factor.

Two key parameters present in Eqns. 3, 4, and 5 above are $$(i) \frac{dZ(t)}{dt_{max}}$$

and (ii) LVET. These parameters are found from features referred to as fiducial points, that are present in the inverted first derivative of the impedance waveform, $$\frac{dZ(t)}{dt}$$

. As described by Lababidi, Z., et al, "The first derivative thoracic impedance cardiogram," Circulation, 41:651–658, 1970, the value of $$\frac{dZ(t)}{dt_{max}}$$

is generally determined from the time at which the inverted derivative value has the highest amplitude, also commonly referred to as the "C point". The value of $$\frac{dZ(k)}{dt_{max}}$$

is calculated as this amplitude value. LVET corresponds generally to the time during which the aortic valve is open. That point in time associated with aortic valve opening, also commonly known as the "B point", is generally determined as the time associated with the onset of the rapid upstroke (a slight inflection) in $$\frac{dZ(t)}{dt}$$

before the occurrence of the C point. The time associated with aortic valve closing, also known as the "X point", is generally determined as the time associated with the inverted derivative global minimum, which occurs after the C point.

In addition to the foregoing "B", "C", and "X" points, the so-called "O point" may be of mitral valve of the heart. The 0 point is generally determined as the time associated with the first peak after the X point. The time difference between aortic valve closing and mitral valve opening is known as the isovolumetric relaxation time, IVRT.

Impedance cardiography further utilizes the subject's electrocardiogram (ECG) in conjunction with the thoracic impedance waveform previously described. Processing of the impedance waveform for analysis generally requires the use of ECG fiducial points as landmarks. Processing of the impedance waveform is typically performed on a beat-by-beat basis, with the ECG being used for beat detection. In addition, detection of some fiducial points of the impedance signal may require the use of ECG fiducial points as landmarks. Specifically, individual beats are identified by detecting the presence of QRS complexes within the ECG. The peak of the R wave (commonly referred to as the "R point") in the QRS complex is also detected, as well as the onset of depolarization of the QRS complex ("Q point").

Historically, the aforementioned fiducial points in the impedance cardiography waveform (i.e., B, C, O, and X points) and ECG (i.e. R and Q points) were each determined through empirical curve fitting. However, such empirical curve fitting is not only labor intensive and subject to several potential sources of error, but, in the case of the impedance waveform, also requires elimination of respiratory artifact. More recently, digital signal processing has been applied to the impedance cardiography waveform for pattern recognition. One mathematical technique used in conjunction with such processing, the well known time-frequency distribution, utilizes complex mathematics and a well known time-frequency distribution (e.g., the spectrogram). See for example, U.S. Pat. Nos. 5,309,917, 5,423,326, and 5,443,073 issued May 10, 1994, Jun. 13, 1995, and Aug. 22, 1995, respectively, and assigned to Drexel University. As discussed in the foregoing patents, the spectrogram is used for extraction of information relating to the transient behavior of the dZ/dt signal. Specifically, a mixed time-frequency representation of the signal is generated through calculation of the Fast Fourier Transform and multiplication by a windowing function (e.g., Hamming function) to convert the one-dimensional discrete dZ/dt signal into a two-dimensional function with a time variable and frequency variable.

However, the spectrogram (and many of the time-frequency distributions in general) suffers from a significant disability relating to the introduction of cross term artifact into the pattern recognition calculations. Specifically, when a signal is decomposed, the time-frequency plane should accurately reflect this signal. If a signal is turned off for a finite time, some time-frequency distributions will not be zero during this time, due to the existence of interference cross terms inherent in the calculation of the distribution.

Another limitation of the spectrogram is its assumption of stationarity within the windowing function. This assumption is valid if the frequency components are constant throughout the window. However, many biological signals, including the ECG and the impedance waveform, are known to be non-stationary.

Additionally, the signal processing associated with such time-frequency distributions by necessity incorporates complex mathematics (i.e., involves operands having both real and imaginary components), which significantly complicates even simple pattern recognition-related computations.

Furthermore, such prior art empirical and time-frequency processing techniques impose substantial filtering requirements which can be restrictive in terms of hardware implementation. For example, the time delay associated with ΔZ waveforms may be large due to factors such as sharp frequency cutoffs required for empirical fiducial point detection.

It is also known that detection of right atrial and ventricular (AV) pacemaker spikes present in the ECG waveform may be useful in cardiovascular analysis. For example, when these spikes are detected, they may act as substitute Q points during definition of the search interval for B, C, and X points within the impedance waveform. Under the common prior art approach, such spikes are identified as a high frequency time derivative in ECG voltage that is larger than a fixed threshold voltage derivative. However, this detection scheme has several disabilities. Specifically, the technique is limited by the minimum spike amplitude that may be detected; i.e., only spikes of certain minimum amplitudes or greater may be detected. Furthermore, high amplitude noise may be misidentified as spikes, thereby reducing the robustness of the technique, especially in comparatively higher noise environments.

Fuzzy Logic and Fuzzy Models

As is well known in the art, so-called "fizzy logic" is a superset of conventional (Boolean) logic that has been extended to handle the concept of partial truth; i.e., truth values falling between "completely true" and "completely false". Fuzzy logic was invented by Dr. Lotfi Zadeh of U.C. Berkeley in 1965. The fuzzy model, which utilizes fuzzy logic, is a problem-solving control system methodology that lends itself to implementation in systems ranging from simple, small, embedded micro-controllers to large, networked, multi-channel PC or workstation-based data systems. It can be implemented in hardware, software, or a combination of both. The fuzzy model provides a comparatively simple technique for arriving at a definite conclusion based upon vague, ambiguous, imprecise, noisy, or missing input information, and in some aspects mimics the human decision making process.

As is well understood in the prior art, a fuzzy model incorporates alternative, rule-based mathematics (e.g., IF X AND Y THEN Z), as opposed to attempting to model a system or its response using closed-form mathematical equations. When the number of model inputs and model outputs are limited to two each, the fuzzy model is in general empirically-based, relying on an empirical data (such as prior observations of parameters or even an operator's experience).

Specifically, a subset U of a set S can be defined as a set of ordered pairs, each with a first element that is an element of the set S, and a second element that is an element of the set $\{0, 1\}$, with exactly one ordered pair present for each element of S. This relationship defines a mapping between elements of S and elements of the set $\{0, 1\}$. Here, the value "0" is used to represent non-membership, and the value "1" is used to represent membership. The truth or falsity of the exemplary statement:

A is in U is determined by finding the ordered pair whose first element is A. The foregoing statement is true if the second element of the ordered pair is "1", and the statement is false if it is "0". Similarly, a fuzzy subset F of set S can be defined as a set of ordered pairs, each having a first element that is an element of the set S, and a second element that is a value falling in the interval [0, 1], with exactly one ordered pair present for each element of S. This defines a mapping between elements of the set S and values in the interval [0, 1]. The value zero is used to represent complete non-membership, the value one is used to represent complete membership, and values in between are used to represent intermediate degrees of membership. These fuzzy subsets serve as the fuzzy inputs and outputs of a fuzzy model, whose input-output relationship is defined by a rule base table.

Inherent benefits of the fuzzy model relate to its speed and simplicity of processing (e.g., MIPS), and its ability to process data that is not easily represented in closed-form equations, such as may occur in physiologic data. However, prior to the present invention, these advantages have not been applied to the analysis of time-variant "noisy" signals where detection and/or identification of one or more artifacts within the waveform against a non-zero noise background of varying amplitude is required, such as electrocardiography, impedance cardiography, or electroencephalography.

Based on the foregoing, what is needed is an improved method and apparatus for waveform assessment, including for example identification of artifacts within electrocardiographs and thoracic impedance waveforms derived from a living subject. Such improved method and apparatus would ideally be accurate, easily adapted to the varying characteristics of different waveforms (and subjects), and would produce reliable results under a variety of different operating conditions and noise environments (i.e., robust). Additionally, such improved method and apparatus would utilize an analytical paradigm, such as fuzzy model, which would reduce the computational load associated with the analysis, thereby further simplifying use in various applications and hardware environments.

SUMMARY OF THE INVENTION

The present invention satisfies the aforementioned needs by an improved method and apparatus for assessing and analyzing waveforms, including physiologic waveforms such as ECGs and thoracic impedance, as well as utilizing the results of such assessment and analysis to obtain other useful information.

In a first aspect of the invention, an improved method of identifying an artifact in a waveform is disclosed. The method generally comprises: providing at least one waveform; determining the shape of the artifact within the waveform; and identifying the artifact based at least in part on the shape. In one exemplary embodiment, the waveform comprises a cardiographic waveform derived from a living subject, and the method comprises identifying one or more right atrial (RA) or right ventricular (RV) pacemaker "spikes" within the waveform using an iterative interval search technique (e.g., golden section search) specifically adapted for this application. Fuzzy analysis is used to identify the relevant noise threshold(s); this threshold is used in conjunction with the aforementioned golden section search to provide robust AV pacing spike detection, which can be used in a number of different applications such as impedance cardiography (ICG).

In a second aspect of the invention, an improved apparatus adapted to identify an artifact in physiologic waveforms from a living subject is disclosed. The apparatus generally comprises: a digital processor adapted to run computer programs thereon; at least one electrode in operative communication with the processor and adapted to provide at least one physiologic waveform from the subject; and a computer program adapted to (i) determine the shape of the artifact within said at least one waveform; and (ii) identify the artifact based at least in part on the shape. In one exemplary embodiment, the second waveform comprises the electrocardiogram (ECG) of the subject, the artifacts comprise individual spikes associated with the AV pacing of the subject's cardiac muscle. A plurality of electrodes are attached to selected points on the subject in order to provide the processor and computer program with the ECG waveform(s).

In a third aspect of the invention, an improved computer program for implementing the aforementioned methods of artifact detection and identification is disclosed. In a first exemplary embodiment, the computer program comprises an object code representation of an assembly language source code listing, the object code representation being disposed on a transportable storage medium (e.g., floppy disk). In a second embodiment, the computer program is disposed on the discrete storage device of a signal processing apparatus and adapted to run on the digital processor thereof. The computer program further comprises a graphical user interface (GUI) operatively coupled to the display and input device of the signal processing apparatus. One or more subroutines or algorithms for implementing the golden section search and noise threshold identification methodologies of the invention are included within the program. These algorithms may also interface with wavelet transform routines within the parent (monitoring) device. In a third exemplary embodiment, the computer program comprises an instruction set disposed within the storage device (such as the embedded program memory) of the digital signal processor (DSP) of the signal processing apparatus.

In a fourth aspect of the invention, an improved method of assessing cardiac output within a living subject is disclosed. The method generally comprises: obtaining at least one cardiographic waveform and at least one impedance waveform from the subject; identifying at least one artifact within the at least one cardiographic waveform based at least in part on shape; and assessing the cardiac output of the subject utilizing the at least one artifact and the impedance waveform. In one exemplary embodiment, the artifacts comprise AV spikes within the ECG of the subject. When these spikes are detected, they may substitute as Q points during definition of the AZ search interval for B, C, and X points within the thoracic impedance waveform.

In a fifth aspect of the invention, improved apparatus adapted to determine the cardiac output of a living subject are disclosed. The apparatus generally comprises: a digital processor adapted to run computer programs thereon; at least one electrode in operative communication with the processor and adapted to provide at least one cardiographic waveform and at least one impedance waveform from the subject; and a computer program adapted to (i) identify at least one artifact within the at least one cardiographic waveform based at least in part on shape; and (ii) assess the cardiac output of the subject utilizing the at least one artifact and the impedance waveform. In one exemplary embodiment, the apparatus includes a digital signal processor (DP) with embedded code adapted to process ECG data obtained from the data to identify AV spikes. A thoracic impedance waveform is also obtained via a plurality of electrodes disposed on the subject. In one variant, these electrodes comprise electrode pairs which have a predetermined spacing. The apparatus may comprise a stand-alone monitor, or alternatively an ICG module adapted for use with other physiologic monitoring or assessment equipment.

In a sixth aspect of the invention, an improved method of providing treatment to a subject using the aforementioned cardiac output assessment methodology is disclosed. The method generally comprises the steps of: disposing a plurality of electrodes with respect to the thoracic cavity of the subject; measuring the impedance and ECG data of the subject non-invasively; identifying at least one artifact within the ECG waveform; determining the cardiac output of the subject based at least in part on the at least one artifact, and providing treatment to the subject based on the determined cardiac output. In one exemplary embodiment, the artifact comprises an AV spike, which is used as an input in determining the stroke volume of the subject's cardiac muscle during at least one cardiac cycle using discrete wavelet transforms.

DETAILED DESCRIPTION OF THE INVENTION

Figure 1:
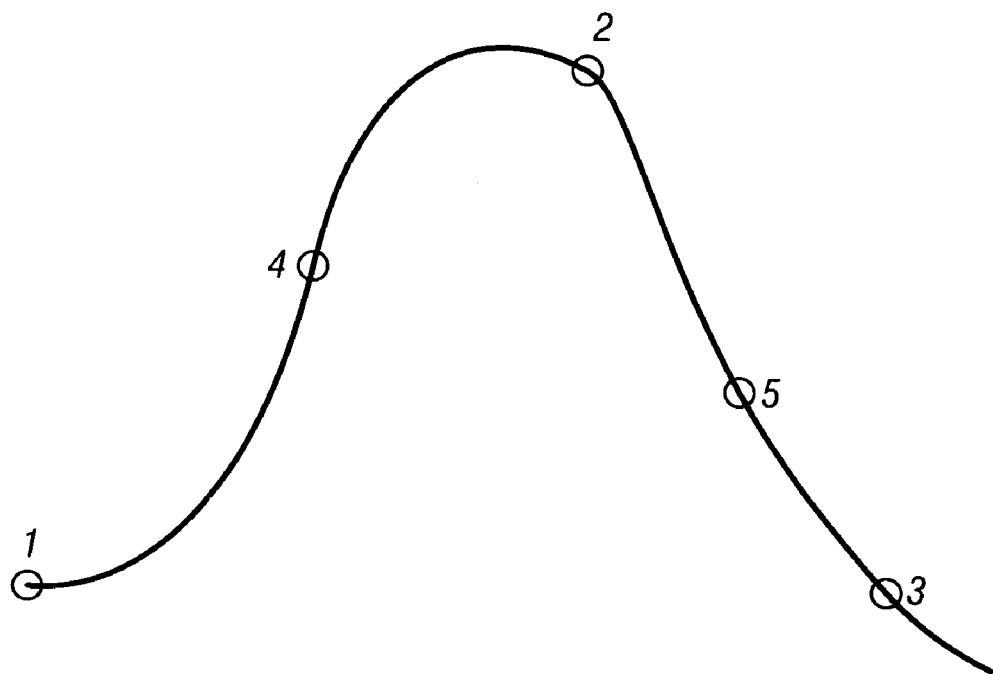
FIG. 1 is a graphical representation of a typical iterative interval (e.g., golden section) search methodology according to the prior art.

Reference is now made to the drawings, wherein like numerals refer to like parts throughout the disclosure.

It is noted that while described primarily in the context of detecting artifacts such as atrial-ventricular (AV) spikes in cardiographic waveforms, the artifact detection and noise characterization methods disclosed herein may be readily adapted to other types of applications, whether physiologic in nature or otherwise. Literally any type of data stream or waveform having artifacts generally of the type described herein may be analyzed using these techniques, including for example acoustic waveforms, or voltage or current waveforms associated with electronic devices. Hence, the invention should in no way be considered limited to cardiographic and ICG analysis, or for that matter physiologic applications.

It is further noted that while the invention is described herein in terms of exemplary apparatus and methods for determining cardiac output suitable for use on the thorax of a human subject, the invention may also be embodied or adapted to monitor cardiac output at other locations on the human body, as well as monitoring cardiac output on other warm-blooded species such as, for example, primates, canines, or porcines. All such adaptations and alternate embodiments are considered to fall within the scope of the claims appended hereto.

Overview

At a fundamental level, the present invention comprises methods and apparatus for detecting artifacts or features with one or more time-variant information streams (e.g., waveforms). In an exemplary embodiment adapted for use in identifying (and utilizing) artifacts in the cardiograms of a human subject, the invention comprises computer code running on a digital processor which is adapted to analyze the subject's ECG waveforms to identify atrial and ventricular pacing spikes. When these spikes are detected, they may substitute as Q points during definition of the AZ search interval for B, C, and X points in a thoracic impedance waveform. Such searches may be conducted using, for example, the wavelet transform model described in co-pending and co-owned U.S. patent application Ser. No. 09/764,589 entitled "Method and Apparatus for Hemodynamic Assessment including Fiducial Point Detection" filed Jan. 17, 2001 which is incorporated herein by reference in its entirety.

Pacing spike detection in the aforementioned exemplary application incorporates some aspects of artificial intelligence, in that it is desirable to detect spikes of varying amplitude, with variable time delays between the A and V spikes, in the presence of noise also having a variable amplitude. This is accomplished using a golden section search optimization technique, in conjunction with a fuzzy model. The golden section search identifies spikes or other artifacts based primarily on their shape as opposed to amplitude or other criteria, thereby significantly increasing the robustness of the detection algorithm.

A fuzzy model is used to calculate the noise threshold, in that a pacemaker spike must be distinguishable from its surrounding noise. Because the spike and noise amplitudes vary with each subject, the noise threshold is calculated in one embodiment during the beginning of a monitoring session, or immediately after a lead change. This noise threshold is then used as an input to the AV spike detector.

Table 1 below provides a summarization of the foregoing parameters related to pacing spike detection and cardiac output determination as used in relation to the present invention.

TABLE 1

| | |
|---|---|
| A | Reference to right atrium |
| B | Sample signifying initial aortic valve opening. |
| C | Sample signifying maximum deflection in the inverse of the first time derivative of ΔZ |
| ΔZ | Time-varying portion of the impedance signal |
| ECG | Electrocardiogram |
| k | Discrete time sample |
| Q | Sample signifying initial left ventricular depolarization |
| V | Reference to right ventricle |
| X | Sample signifying aortic valve closure |

Figure 2:
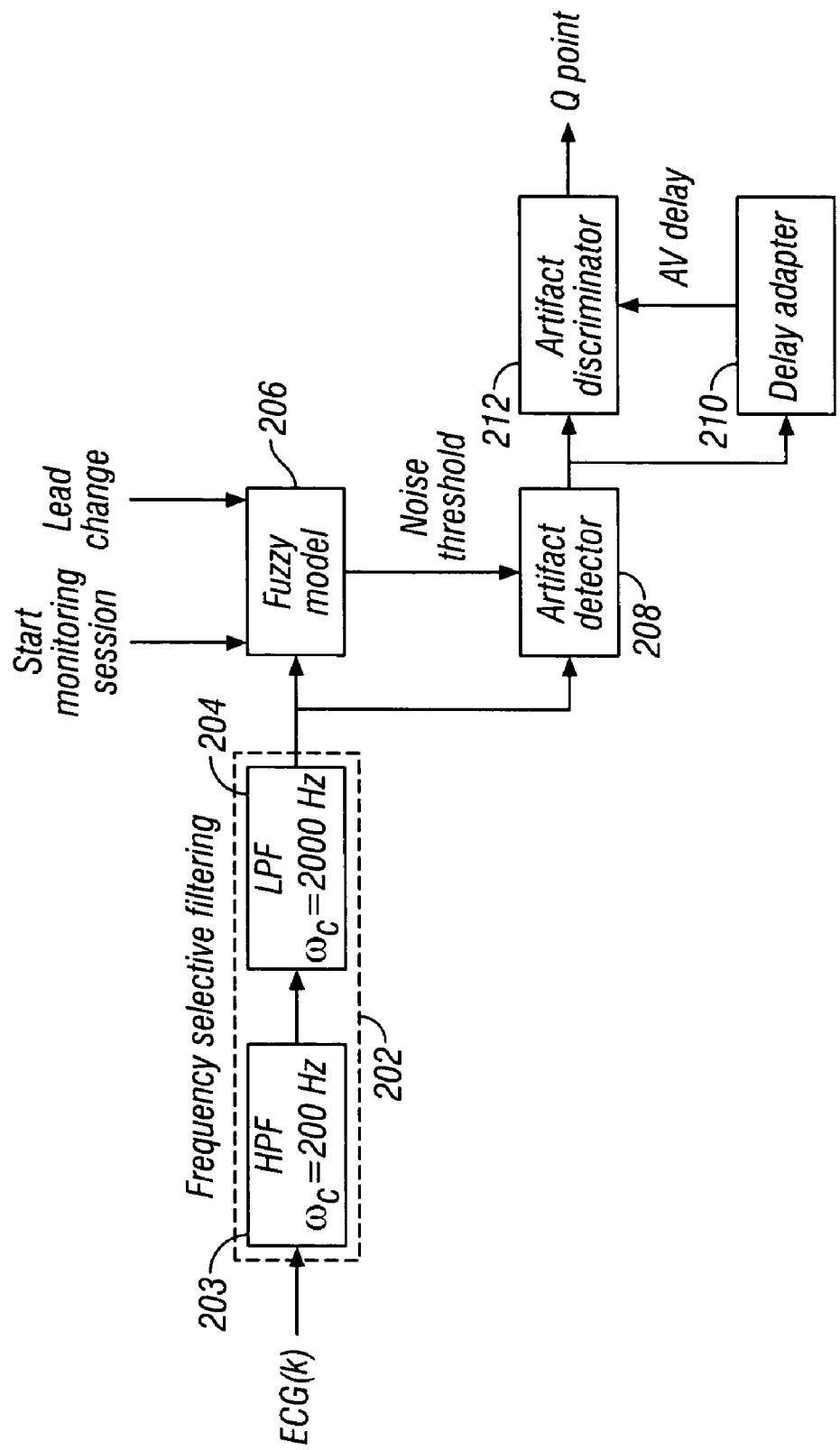
FIG. 2 is a block diagram illustrating one exemplary embodiment of the methodology of assessing a time variant waveform according to the present invention.
Figure 2A:
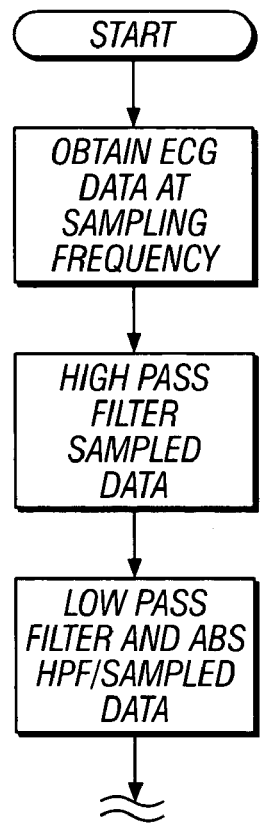
FIG. 2a is a logical flow diagram one exemplary embodiment of waveform data filtering according to the present invention.
Figure 2B:
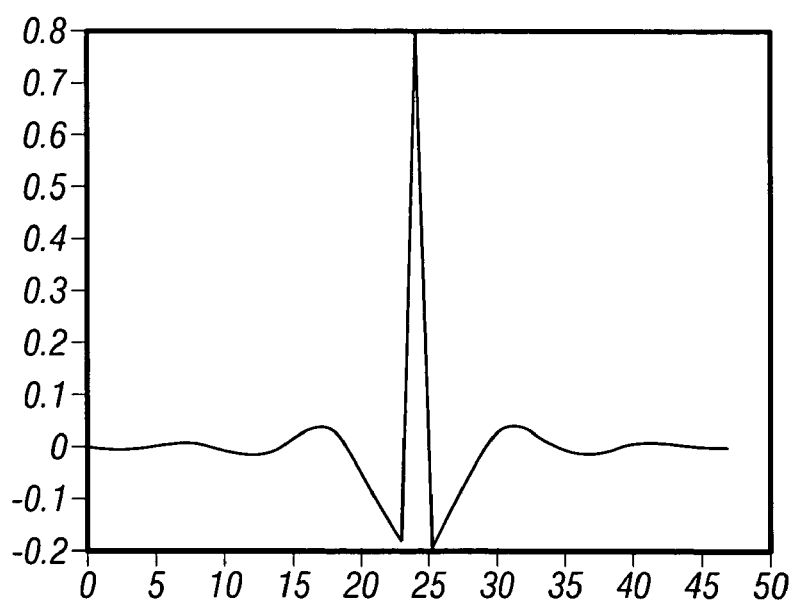
FIGS. 2b and 2c are graphical representations of highpass filter impulse response and magnitude response, respectively, according to an exemplary embodiment of the invention.
Figure 2C:
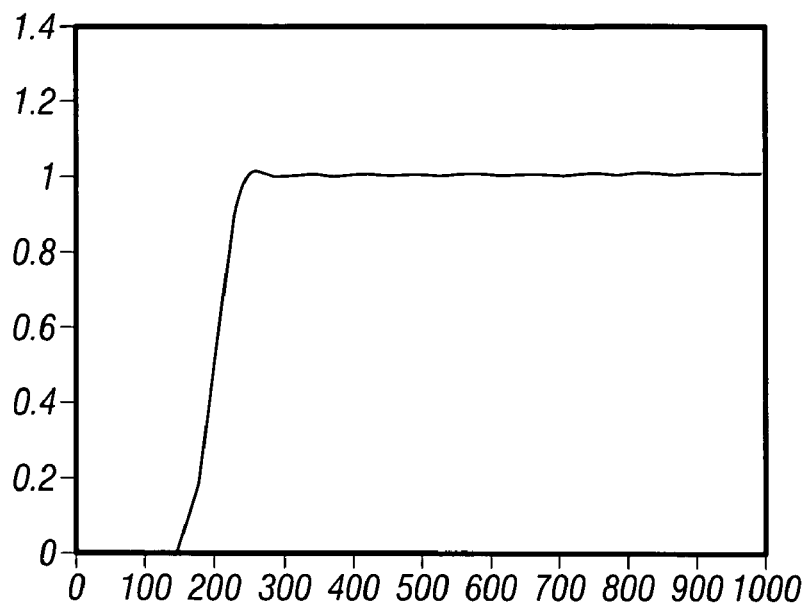
Figure 2D:
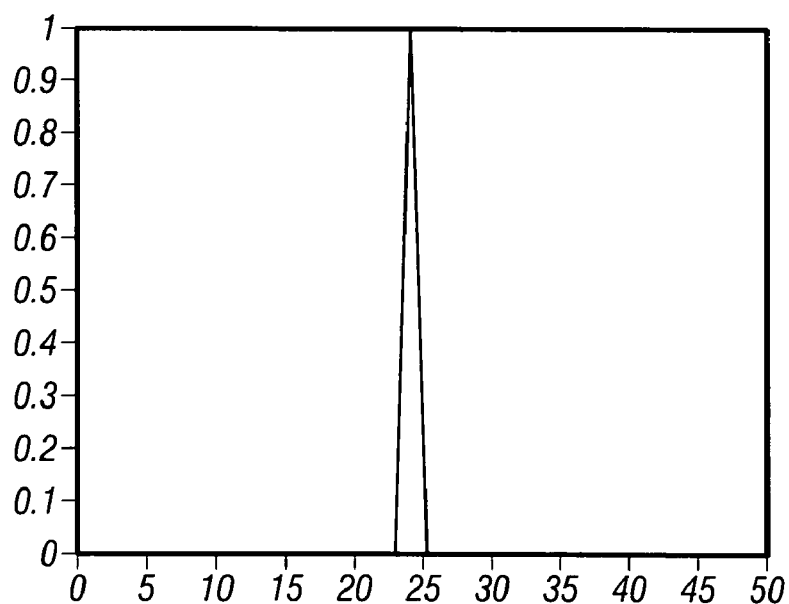
FIG. 2d is a graphical representation of lowpass filter impulse response according to an exemplary embodiment of the present invention.
Figure 2E:
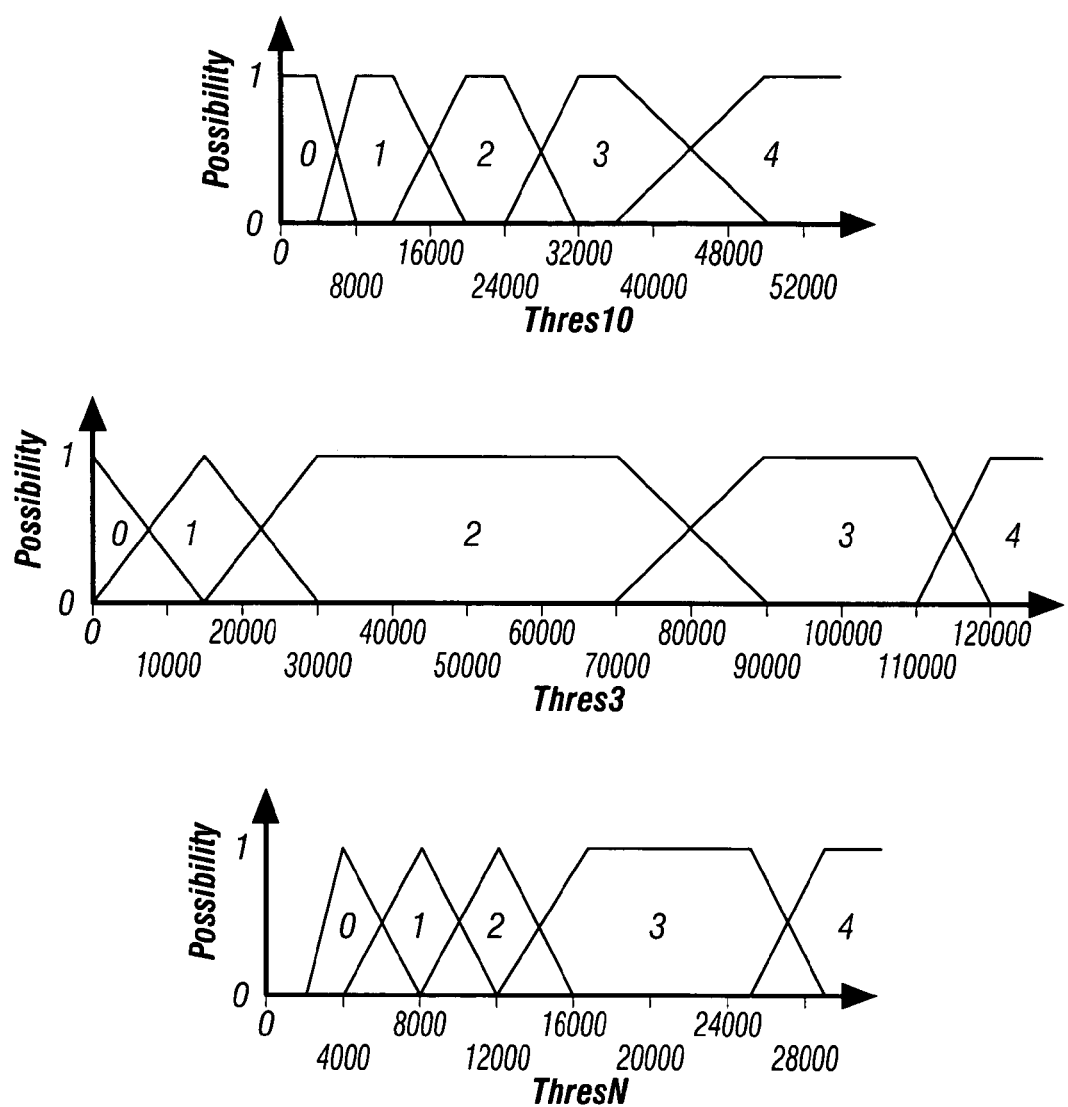
FIG. 2e is a graphical representation of exemplary input membership functions for Thres10 and Thres3, and exemplary output membership functions for ThresN.
Figure 2F:
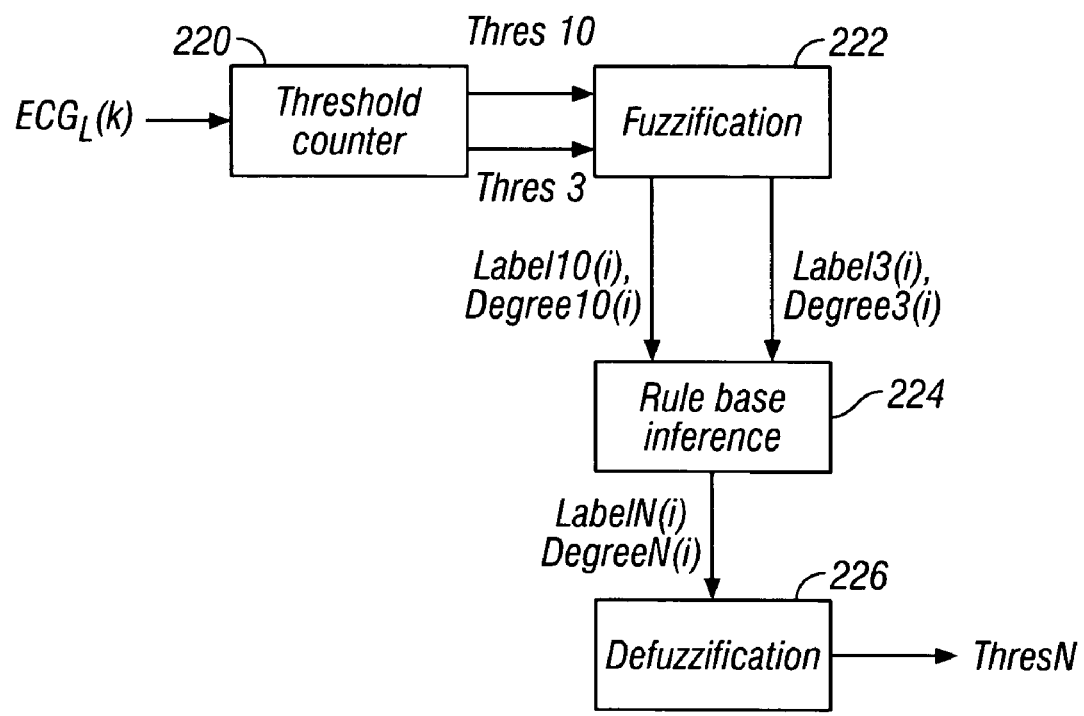
FIG. 2f is a block diagram illustrating the interconnectivity between constituent modules in an exemplary embodiment of the noise threshold detector module of FIG. 2.
Figure 2G:
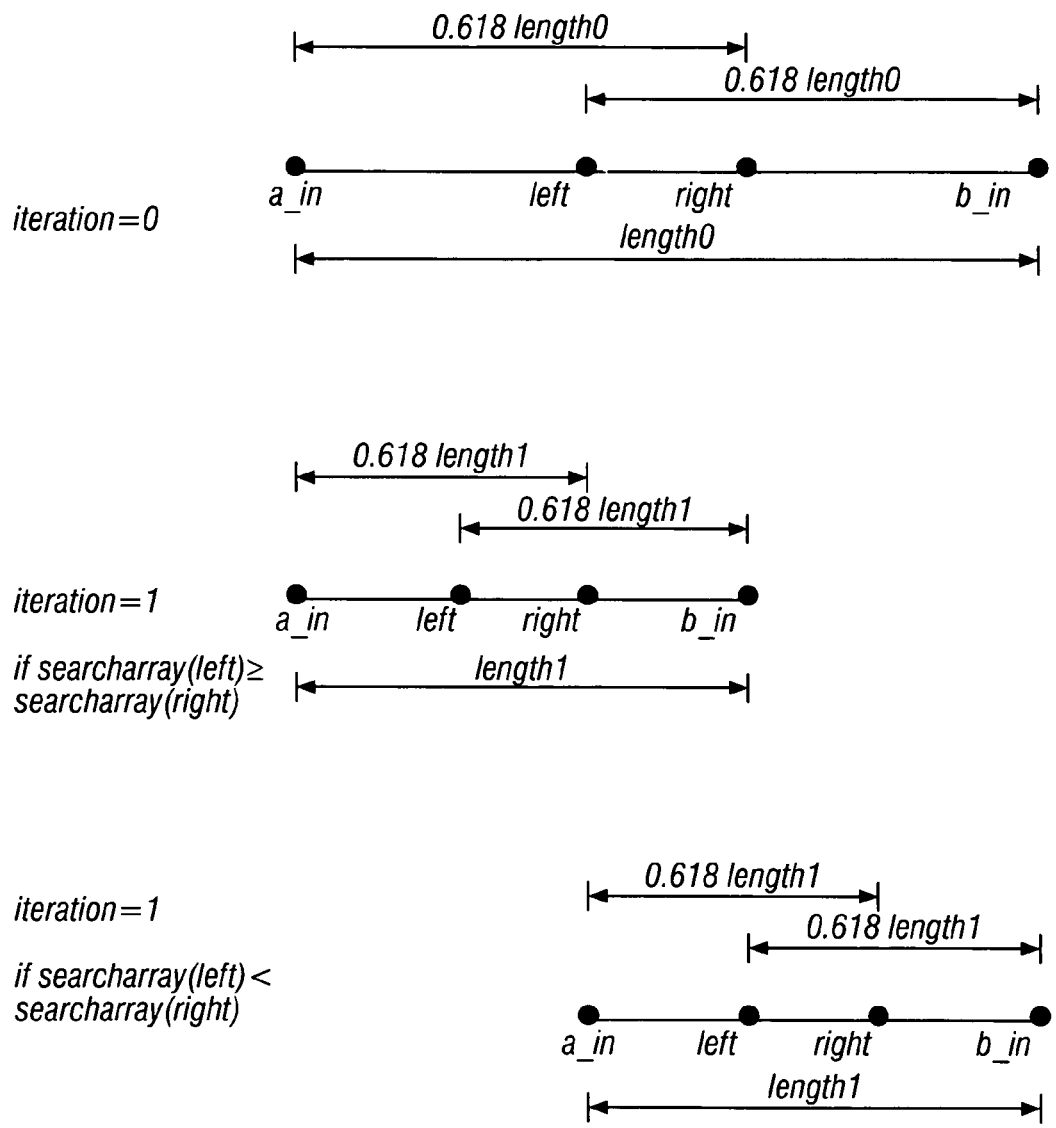
FIG. 2g is a graphical representation of the methodology of iterative interval search (first two iterations only) according to one exemplary embodiment of the invention.

Referring now to FIGS. 2–2g, one exemplary embodiment of the method 200 of data analysis according to the present invention is described. In this exemplary embodiment (FIG. 2), the methodology can be represented as five (5) functional "modules" used to perform the analysis, including (i) the frequency selective filtering module 202; (ii) the noise threshold module 206; (iii) the artifact detector module 208; (iv) delay adapter module 210, and (v) artifact discriminator module 212. A sixth module, the pace module (not shown), is also optionally utilized with the foregoing five modules 202, 206, 208, 210, 212 when the detected AV spike is substituted for the Q point in the ECG waveform, as discussed in greater detail below.

These modules are now described in detail. For the purposes of the following discussion, it is assumed that 800 samples of ECG data are added to an ECG buffer during each algorithm iteration. When a Q point is found in the ECG or when an A or V spike location is substituted for the Q point the samples preceding and including this Q point, are deleted from the buffer before the next iteration. It will be recognized, by those of ordinary skill in the signal processing arts, however, that other approaches (e.g., buffering and/or sample sizes) may be utilized consistent with the broader invention disclosed herein.

Frequency Selective Filtering —Pacing spike detection in the illustrated embodiment is accomplished using, inter alia, highpass filtered ECG signals. The ECG signal is sampled at 2000 Hz, highpass filtered at a cutoff frequency of 200 Hz to isolate pacing spikes from lower frequency R waves, and then lowpass filtered at a cutoff frequency of 1000 Hz to minimize the distortion of high frequency noise. FIG. 2a illustrates this methodology generally.

The highpass filter 203 is in the instant embodiment of the filter module 202 comprises a Kaiser window of the type well known in the electronic arts having cutoff frequency of 200 Hz, a stopband of 150 Hz, a passband of 250 Hz, and a ripple of 1%. The impulse response and dmagnitude response of this exemplary filter are shown in FIGS. 2b and 2c, respectively. Inputs to the filter are ECG(k), the ECG waveform, digitized with a sampling frequency of 2000 Hz; and $b_{H0}$–$b_{H46}$, the highpass filter coefficients (shown in Table 2).

TABLE 2

| $b_{H0}$ to $b_{H15}$ | $b_{H16}$ to $b_{H31}$ | $b_{H32}$ to $b_{H46}$ |
|---|---|---|
| −0.0019 | 0.0378 | 0.0166 |
| −0.0026 | 0.0283 | 0 |
| −0.002 | 0 | −0.0121 |
| 0 | −0.0448 | −0.0168 |
| 0.0031 | −0.0985 | −0.0143 |
| 0.0061 | −0.1497 | −0.0076 |
| 0.0074 | −0.1866 | 0 |
| 0.0054 | 0.8 | 0.0054 |
| 0 | −0.1866 | 0.0074 |
| −0.0076 | −0.1497 | 0.0061 |
| −0.0143 | −0.0985 | 0.0031 |
| −0.0168 | −0.0448 | 0 |
| −0.0121 | 0 | −0.002 |
| 0 | 0.0283 | −0.0026 |
| 0.0166 | 0.0378 | −0.0019 |
| 0.0317 | 0.0317 | |

Outputs of the highpass filter module are $ECG_H(k)$, or the highpass filtered ECG waveform. This waveform is calculated from the input, ECG(k), using standard convolution, as shown in Eqn. (6) below:

$$ECG_H(k)=b_{H0}ECG(k)+b_{H1}ECG(k-1)+ \ldots +b_{H46}ECG(k-46). \quad \text{Eqn. (6)}$$

The lowpass filter 204 of the first module 202 is also a Kaiser window, yet with cutoff frequency of 1000 Hz, a stopband of 950 Hz, a passband of 250 Hz, and a ripple of 1%. The filter's impulse response is shown in FIG. 2d. Input parameters to the lowpass filter 204 include $ECG_H(k)$, the highpass filtered ECG waveform, and $b_{23}=1$, the only non-zero lowpass filter coefficient.

An internal variable, $ECG_{TEMP}(k)$, comprising the lowpass filtered ECG waveform, is calculated from $ECG_H(k)$, using standard convolution as shown in Eqn. (7) below:

$$ECG_{TEMP}(k)=ECG_H(k-23). \quad \text{Eqn. (7)}$$

Output from the lowpass filter 204 (and hence the filter module 202) comprises $ECG_L(k)$, the absolute value of the lowpass filtered ECG. The absolute value is taken to transform any pacemaker spikes present in the filtered ECG into approximately unimodal functions. This signal is input to the next module, the noise threshold module 206.

Noise Threshold Module—A spike or other artifact within a waveform must be distinguishable from its surrounding noise, especially in the context of an AV pacing spike in an ECG. Because the amplitude of the AV pacing spike(s) and the amplitude of the noise vary with each subject, the current noise threshold is calculated (i) during the beginning of a monitoring session, and/or (ii) immediately after a change of electrical lead configuration. This noise threshold is then used as an input to the spike detection module described subsequently herein.

The noise threshold is, in the illustrated embodiment, estimated from 10,000 samples ($10^4$, representing 5 seconds) of $ECG_L(k)$ data, at the start of a monitoring session, or after the ECG lead has been changed, using a fuzzy model. The inputs to the fuzzy model are the threshold at which count=$n_1$ is crossed, represented by the variable $Thresn_1$ (e.g., Thres10, where $n_1$=10 in the present embodiment) and the threshold at which count=$n_2$ is crossed, $Thresn_2$ (Thres3 in the present embodiment). The fuzzy model output is the noise threshold, ThresN. The input and output membership functions associated with the exemplary fuzzy model are shown in FIG. 2e.

The interconnectivity between constituent modules in the noise threshold detector module 206 is shown in FIG. 2f. The threshold counter 220 enables calculation of crisp (i.e., non-fuzzy) inputs to the fuzzy model. These inputs are transformed through a fuzzification process 222, which utilizes the input membership functions, to produce fuzzy inputs. The fuzzy inputs are mapped to fuzzy outputs using a Rule Base Inference (RBI) process 224, although other fuzzy input/output mapping or correlation schemes may be substituted. Through a defuzzification process 226, which utilizes the output membership function, the crisp noise threshold value is determined. Each of these functional components is now described in detail.

Input parameters to the threshold counter 220 include $ECG_L(k)$, comprising 10,000 ($10^4$) samples of the lowpass filtered ECG waveform. Internally, the threshold counter 220 generates a count array variable Count(i,j). This count array provides a count of the number of samples that exceed a certain threshold. The threshold value is recorded in a first column (0), while the corresponding count is recorded in a second column (1). This array is calculated using the following exemplary algorithm (written in pseudocode):

Output parameters associated with the threshold counter 220 of the instant embodiment include (i) Thres10, the minimum threshold with at least 10 peaks, which is calculated using the following pseudocode algorithm:

```
length=ROWSIZE(count);     /* calculate length of row in array */
i = -1;
while (length > i AND count(i,1) <= 10)
    i++;
if (length > i)
    Thres10 = count(i,0);
else
    Thres10 = 0;
``` and Thres3, the minimum threshold with at least 3 peaks, which is calculated using the following pseudocode algorithm:

```
i = -1;
while (length > i AND count(i,1) <= 3)
    i++;
if (length > i)
    Thres3 = count(i,0);
else
    Thres3 = 0;
```

As previously stated, the crisp inputs shall be translated through membership functions into fuzzy inputs as part of the fuzzification process 222. Input parameters for the fuzzification process include the two aforementioned variables, Thres10 and Thres3.

The fuzzification process 222 also utilizes two internal variables, T10 and T3. T10 comprises the low resolution Thres10 threshold. T10 is calculated according to Eqn. (8):

$$T10 = INT(Thres10/4000), \qquad \text{Eqn. (8)}$$

where T10 is bounded within the range {0,13}. T3, the low resolution Thres3 threshold, is calculated according to Eqn. (9):

$$T3 = INT(Thres3/5000). \qquad \text{Eqn. (9)}$$

```
index=0;
maximum=MAX(ECGL);         /* find maximum in ECGL(k) */
while (maximum>5000) {
    If (maximum > 10000){
        If (maximum > 100000) {
            decrement=20000;
            thres = INT(maximum/decrement)*decrement
        }
        else {
            decrement = 10000;
            thres = INT(maximum/decrement)*decrement;
        }
    else {
        decrement = 1000;
        thres = INT(maximum/decrement)*decrement;
    }
    count(index,0)thres;
    count(index, 1)=COUNT#SAMPLESGREATERTHANOREQUALTOTHRES(ECGL);
    maximum = thres – decrement;
}
  © Copyright 2002 CardioDynamics International Corporation. All rights reserved.
```

T3 is bounded within the range {0,24}. Output parameters associated with the fuzzification process 222 include the following:

- Label10(i)—One or two labels associated with Thres10, based on Table 3 below.
- Degree10 (i)—The degree associated with each Thres10 label, based on Table 4 below.
- Label3(i)—One or two labels associated with Thres3, based on Table 5 below.
- Degree3(i)—The degree associated with each Thres3 label, based on Table 6 below.

TABLE 3

| T10 | Label10(0) | Label10(1) |
|---|---|---|
| 0 | 0 | |
| 1 | 0 | |
| 2 | 1 | |
| 3 | 1 | |
| 4 | 1 | 2 |
| 5 | 2 | |
| 6 | 2 | |
| 7 | 2 | 3 |
| 8 | 3 | |
| 9 | 3 | |
| 10 | 3 | 4 |
| 11 | 3 | 4 |
| 12 | 3 | 4 |
| 13 | 4 | |

TABLE 4

| T10 | Degree10(0) | Degree10(1) |
|---|---|---|
| 0 | 1 | |
| 1 | 1 | |
| 2 | 1 | |
| 3 | 1 | |
| 4 | 0.5 | 0.5 |
| 5 | 1 | |
| 6 | 1 | |
| 7 | 0.5 | 0.5 |
| 8 | 1 | |
| 9 | 1 | |
| 10 | 0.75 | 0.25 |
| 11 | 0.5 | 0.5 |
| 12 | 0.25 | 0.75 |
| 13 | 1 | |

TABLE 5

| T3 | Label3(0) | Label3(1) |
|---|---|---|
| 0 | 0 | |
| 1 | 0 | 1 |
| 2 | 0 | 1 |
| 3 | 1 | |
| 4 | 1 | 2 |
| 5 | 1 | 2 |
| 6 | 2 | |
| 7 | 2 | |
| 8 | 2 | |
| 9 | 2 | |
| 10 | 2 | |
| 11 | 2 | |
| 12 | 2 | |
| 13 | 2 | |
| 14 | 2 | |
| 15 | 2 | 3 |
| 16 | 2 | 3 |
| 17 | 2 | 3 |
| 18 | 3 | |
| 19 | 3 | |

TABLE 5-continued

| T3 | Label3(0) | Label3(1) |
|---|---|---|
| 20 | 3 | |
| 21 | 3 | |
| 22 | 3 | |
| 23 | 3 | 4 |
| 24 | 4 | |

TABLE 6

| T3 | Degree3(0) | Degree3(1) |
|---|---|---|
| 0 | 1 | |
| 1 | 0.67 | 0.33 |
| 2 | 0.33 | 0.67 |
| 3 | 1 | |
| 4 | 0.67 | 0.33 |
| 5 | 0.33 | 0.67 |
| 6 | 1 | |
| 7 | 1 | |
| 8 | 1 | |
| 9 | 1 | |
| 10 | 1 | |
| 11 | 1 | |
| 12 | 1 | |
| 13 | 1 | |
| 14 | 1 | |
| 15 | 0.75 | 0.25 |
| 16 | 0.5 | 0.5 |
| 17 | 0.25 | 0.75 |
| 18 | 1 | |
| 19 | 1 | |
| 20 | 1 | |
| 21 | 1 | |
| 22 | 1 | |
| 23 | 0.5 | 0.5 |
| 24 | 1 | |

The Rule Based Inference(RBI) process 224 comprises a Zadeh intersection of the type well known in the art in order to obtain fuzzy outputs. Input parameters to the RBI process 224 include:

- Label10(i)—One or two labels associated with Thres10.
- Degree10(i)—The degree associated with each Thres10 label.
- Label3(i)—One or two labels associated with Thres3.
- Degree3(i)—The degree associated with each Thres3 label.

Output parameters associated with the RBI process 224 include the following:

- LabelN(i)—One to four labels associated with ThresN. Each combination of Label10(i) and Label3(i) is input to Table 7 below to determine LabelN(i).
- DegreeN(i)—The degree associated with each ThresN label. For each combination of Label10(i) and Label3(i), the minimum associated Degree10(il) or Degree3(i) is output as DegreeN(i).

TABLE 7

| | Label3(i) | | | | |
|---|---|---|---|---|---|
| Label10(i) | 0 | 1 | 2 | 3 | 4 |
| 0 | 0 | 1 | 1 | 1 | 1 |
| 1 | 1 | 1 | 2 | 2 | 2 |
| 2 | 2 | 2 | 2 | 3 | 4 |
| 3 | 3 | 3 | 3 | 3 | 4 |
| 4 | 4 | 4 | 4 | 4 | 4 |

The fuzzy outputs described above are processed in the defuzzification process 226 to a crisp output using the well-known centroid method. Input parameters to the defuzzification process 226 include:

LabelN(i)—One to four labels associated with ThresN.

DegreeN(i)—The degree associated with each ThresN label.

MF(i,j)—Membership functions for ThresN. The row represents the label 0–4. The column represents the membership function sample. This array is shown in Table 8.

TABLE 8

| Mem. Func. | Sample | | | | | | | | | | | | | | |
|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 |
| 0 | 0 | 1 | 0.5 | 0 | 0 | 0 | 0 | 0 | 0 | 0 | 0 | 0 | 0 | 0 | 0 |
| 1 | 0 | 0 | 0.5 | 1 | 0.5 | 0 | 0 | 0 | 0 | 0 | 0 | 0 | 0 | 0 | 0 |
| 2 | 0 | 0 | 0 | 0 | 0.5 | 1 | 0.5 | 0 | 0 | 0 | 0 | 0 | 0 | 0 | 0 |
| 3 | 0 | 0 | 0 | 0 | 0 | 0 | 0.5 | 1 | 1 | 1 | 1 | 1 | 1 | 0.5 | 0 |
| 4 | 0 | 0 | 0 | 0 | 0 | 0 | 0 | 0 | 0 | 0 | 0 | 0 | 0 | 0.5 | 1 |

Internal parameters generated within the defuzzification process 226 include F(j), the fuzzification union function. This variable represents the union of the individual membership functions, with associated degrees, as given by Eqn. (10):

$$F(j) = \text{clip}\{\text{DegreeN}(0), MF[\text{LabelN}(0), :]\} \cup \text{clip}\{\text{DegreeN}(1)\, MF[\text{LabelN}(1), :]\}$$

$$\cup \text{clip}\{\text{DegreeN}(2), MF[\text{LabelN}(2), :]\} \cup \text{clip}\{\text{DegreeN}(3), MF[\text{LabelN}(3), :]\}, \quad \text{Eqn. (10)}$$

where the convention ":" refers to using all indices j=0 to 15, and the convention clip[x,y(j)] refers to clipping all values of the function y(j) at the maximum value of x.

The output of the defuzzification process 226 of FIG. 2e is the sole variable ThresN, or the noise threshold. ThresN is found from calculating the centroid of the fuzzification union according to Eqn. (11):

$$ThresN = \frac{\sum_{j=0}^{14} F(j) \cdot (2000j + 2000)}{\sum_{j=0}^{14} (2000j + 2000)}. \quad \text{Eqn. (11)}$$

Note that the factor of 2000 present in the above embodiment of the invention is based on the resolution of the crisp output x axis in FIG. 2e. It will be recognized by those of ordinary skill, however, that the Eqn. (6) can be generalized and readily utilized in other applications.

Artifact Detector—Traditionally, an artifact such as an ECG spike is identified as a high frequency time derivative in ECG voltage that is larger than a fixed threshold voltage derivative. As previously described, this traditional detection scheme is limited by the minimum spike amplitude that may be detected and by the misidentification of high amplitude noise as spikes. In contrast, the exemplary algorithm(s) of the present invention detect spikes strictly by shape, which enables spikes of variable amplitude to be detected. In the illustrated embodiment, a golden section search identifies these spike shape(s).

$ECG_L(k)$ samples are input to the artifact detector in groups of Bufferlength=800 samples. Pacemaker spikes within these samples are detected using the golden section search module or process, as called by the array parser process, and sent to the AV discriminator module 212 for selection of a substitute Q point. During the golden section search, two points at which function values are compared are symmetrically located in the search interval during each search iteration. The uncertainty interval length is reduced by a fixed rate of 0.618, the so-called "golden ratio," during each search iteration. It will be recognized, however, that other values (whether fixed or variable) may be substituted for this value based on the particular application and properties desired. The first two iterations of this exemplary process are illustrated in FIG. 2g.

Within the exemplary array parser process, samples are processed in groups of Loop=30 because this corresponds to the minimum number of samples between pacing spikes at 2000 Hz. The typical range of right AV delay settings in current pacemakers is between 15 and 300 msec. Input parameters to the exemplary array parser process include the following:

$ECG_L(K)$—Lowpass filtered, absolute value ECG waveform

ThresN—Noise threshold

Bufferlength—Subset of lowpass filtered ECG samples to be processed (800 samples in the present embodiment)

Loop—The minimum number of samples between pacemaker spikes (30 samples in the present embodiment).

The array parser process generates an internal parameter Spikes(k), which is the array containing spike identification information. The following designations are used in conjunction with the Spikes(k) variable:

−100=no spike,

+1000=spike, plus additional samples.

This array is constructed using the following pseudocode algorithm:

```
detection = 1000;
nodetection = -100;
Spikes = EMPTY;      /* at initialization this array has no elements */
data = ECGL;         /* data array contains ECGL(k) subset data to be processed */
```

-continued

```
while (LENGTH(data) >0) {
test = data(0: (Loop-1) )
thres = ThresN;
Possible = COUNT#SAMPLESGREATERTHANOREQUALTOTHRES(test);
/* determine locations of localized peaks */
Locationarray                                                            =
  SAMPLELOCATIONSATWHICHVALUESGREATERTHANOREQUALTOTHRES(test);
if (Possible > 0) {
    array1 = data( (Locationarray(0) - 4): (Locationarray(0)+Loop-5) );   /*find beginning of
search */
    arrayr = REVERSE(array1); /* reverse order of array1 for further processing */
    i=0;
    while (arrayr(i) <= thres)
        i++;
    Searcharray = array1((Locationarray(0) - 4) : (Locationarray(0) -5 + Loop -i) );
    Maxlocation = GOLDENSECTIONSEARCH(Searcharray);   /*See Section 8.2 */
    /* create array of values "nodetection" of length(Locationarray(0)-4) */
    beforepeakarray = CREATEARRAY(nodetection, Locationarray(0)-4);
    Spikes = CONCATENATEARRAYS(Spikes, beforepeakarray);
    peakarray = CREATEARRAY(nodetection, Loop*2);
    Spikes = CONCATENATEARRAYS(Spikes,peakarray);
    data =UPPERSPLIT(data(Locationarray(0)-4+2*Loop));   /*isolate array past peak for future
use */
    }
else
    data = UPPERSPLIT(Loop);
}
```

© Copyright 2002 CardioDynamics International Corporation. All rights reserved.

Output parameters associated with the array parser process include Spikearray(k), the subset of the Spikes array, which is defined as Spikes(0:Bufferlength-1).

The golden section search process of the invention is now described. Input parameters to this process include Searcharray(k), which is a subset of the ECGL(K) array in which the maximum value and maximum value location are determined. Internally, the variable Maxvalue is generated, which comprises the maximum value within Searcharray(k) and is determined using the following exemplary golden search optimization algorithm (written in pseudocode):

```
searchint=4;
a_in = 0;
b_in = LENGTH(searcharray) - 1;
while(searchint > 3){
    temp = 0.618*(b_in - a_in +1);
    left = b_in - temp;
    right = a_in + temp;
    if (searcharray(left) >= searcharray(right) )
        b_in = right;                      /* keep a_in as is */
    else
        a_in = left;                       /* keep b_in as is */
    searchint = b_in - a_in +1;            /* new length of search interval for peak */
    }
searchintervalarray = searcharray(a_in:b_in);   /* define final search interval for max value
*/
Maxvalue = MAX(searchintervalarray);
```

© Copyright 2002 CardioDynamics International Corporation. All rights reserved.

The golden section search process outputs the Maxlocation variable, which is the location within Searcharray(k) corresponding to the maximum value. This value is determined as the sum of (location of maximum in searchintervalarray+ a_in).

Delay Adapter—Initially, the AV delay value (Avdelay) is defaulted to 350 msec., based on observation of data from over two hundred patients. However, with the appearance of a particular feature (e.g., a particular pattern of spikes in the ECG waveform), the AV delay is dynamically lengthened to a more appropriate value.

During each iteration, Avdelay is reevaluated and, if necessary, adjusted. If Avdelay is correct, then no pacemaker spike will be present in the first 700 samples of Spikearray (k). Recall that when a Q point is found or spike is designated as a Q point, all samples preceding and including this Q point are deleted from the buffer. Inputs to the exemplary delay adapter process include:

Spikearray(k)—Array containing spike identification information.

Oldavdelay—Adaptive AV delay from most recent iteration. The default value is set to 700 samples (350 msec).

The delay adapter process also generates the following internal parameters:

Number—The number of spikes detected within Spikearray(0:699).

Locationarray—An array containing the sample locations of spike spikes detected within Pacearray(0:699).

The outputs of the delay adapter process comprises Avdelay, the new adaptive AV delay. If Number=1, then Avdelay is recalculated according to Eqn. (12):

$$AVdelay=Locationarray(1)-Locationarray(0)+30. \quad \text{Eqn. (12)}$$

Otherwise, Avdelay=oldavdelay.

Artifact Discriminator—Once AV spikes have been identified, they are classified as being either right atrial or right ventricular spikes. In the present embodiment, it is assumed that at most two types of spikes are present. In other words, it is assumed that left ventricular spikes, which can be important to chronic resynchronization pacing therapy in congestive heart failure patients, are not present. If only an atrial or ventricular spike is present, this spike is designated as the Q point. If both atrial and ventricular spikes are present, the ventricular spike is designated as the Q point. Atrial and ventricular spikes are distinguished by the AV delay between them.

For each beat, the most recent spike is designated as the Q point. A and V spikes in the same beat are identified by their AV delay relationship. Inputs to the discriminator process 212 of FIG. 2 include:

Spikearray(k)—Array containing the spike identification information.

Avdelay—Adaptive AV delay.

Internal parameters generated by the discriminator process comprise the following:

Possible—Count of samples greater than or equal to threshold=1000 in Pacearray(k)

Locationarray(i)—Sample locations where values in Pacearray(k)$\geq$1000;

The outputs of the discriminator module 212 is the SubQarray parameter, which comprises an array containing code values for spike identification. The codes used in the exemplary embodiment are as follows:

1000 = spike found that may substitute for Q point,
−100 = no substitute Q point,
−1000 = possible substitute Q point that will be reevaluated during next iteration.

SubQarray is calculated using the following exemplary pseudocode algorithm:

```
nodetection = -100;
postponedetection = -1000;
SubQarray=Spikearray;
if (Possible <2) {              /* process 0 or 1 A or V spikes */
    if( Possible = 1){          /* if no spikes found, no operations take place */
        if ( LENGTH(Spikearray) - Locationarray(0) ) > Avdelay)
            ;   /* most recent spike in beat found, so keep labelled as spike/
        else
            SubQarray(Locationarray(0)) = postponedetection; /*delay decision till next iteration */
        }
else {
    index = 0;
    while (index < Possible - 1) {
        if( Locationarray(index+1) - Locationarray(index) > Avdelay)
            index++;       /* both spikes are viable Q points */
        else {      /* A and V spikes in same beat, so just have V as substitute Q */
            SubQarray (Locationarray(index))= nodetection;
            index = index + 2;
            }
        }
    if (index <= Possible - 1){       /*check for last spike to process */
        if (LENGTH(Spikearray) - Locationarray(index) <= Avdelay)      /* if spike exists, process */
            /*delay spike decision till next iteration*/
            subQarray(Locationarray(index)) = postponedetection;
            }
    }
    © Copyright 2002 CardioDynamics International Corporation. All rights reserved.
```

It is noted that the exemplary AV pacing spike detection algorithms described above were developed and tested from actual data obtained from living subjects. Specifically, data from 167 pacing patients were used to identify a general detection strategy of a combined fuzzy model and golden section search. Later, 3 beats each of 57 waveforms from 14 pacing patients were used as training sets; 3 beats each of 63 waveforms from 14 other pacing patients were used as initial testing sets. For each patient, the baseline waveform, and when possible, waveforms from other pacemaker settings were saved. The other pacemaker settings consisted of unipolar pacing at two settings (maximum amplitude and pulse width, minimum amplitude and pulse width) and bipolar pacing at two settings (maximum amplitude and pulse width, minimum amplitude and pulse width). Because patient response to these other pacemaker settings is so varied, these 120 training and testing waveforms simulated waveforms from 120 patients. The mean absolute error (MAE) for substitute Q point spike detection in the training data was 0 samples. The MAE for substitute Q point spike detection in the testing data was 4 samples. However, spikes were mis-detected in all 12 beats in 4 waveforms from one testing patient because the default AV delay detection window was too small (650 samples), resulting in a MAE of 69 samples for that patient alone. When the detection window was lengthened to 700 samples, the MAE for that patient decreased to 0 samples. Notably, for the other beats in 13 testing patients, the MAE with the original AV delay detection window was 0 samples.

It is further noted that the waveform assessment methodology of the present invention may be applied to other signals besides electrocardiograms. For example, the combination of electroencephalography (EEG) and functional magnetic resonance imaging (fMRI) is now being used to analyze brain function. However, ballistocardiogram artifact, which is caused by the pulsatile motion related to the cardiac cycle, dominates the EEG signal in the MR environment. These ballistocardiogram artifacts, which resemble "spikes" after the absolute value is taken, may be removed using the methods disclosed herein. The invention may be beneficially employed in yet other applications having similar spike-like artifact, such use being readily accomplished by those of ordinary skill in the biomedical electronics arts given the disclosure provided herein.

Apparatus

Figure 3:
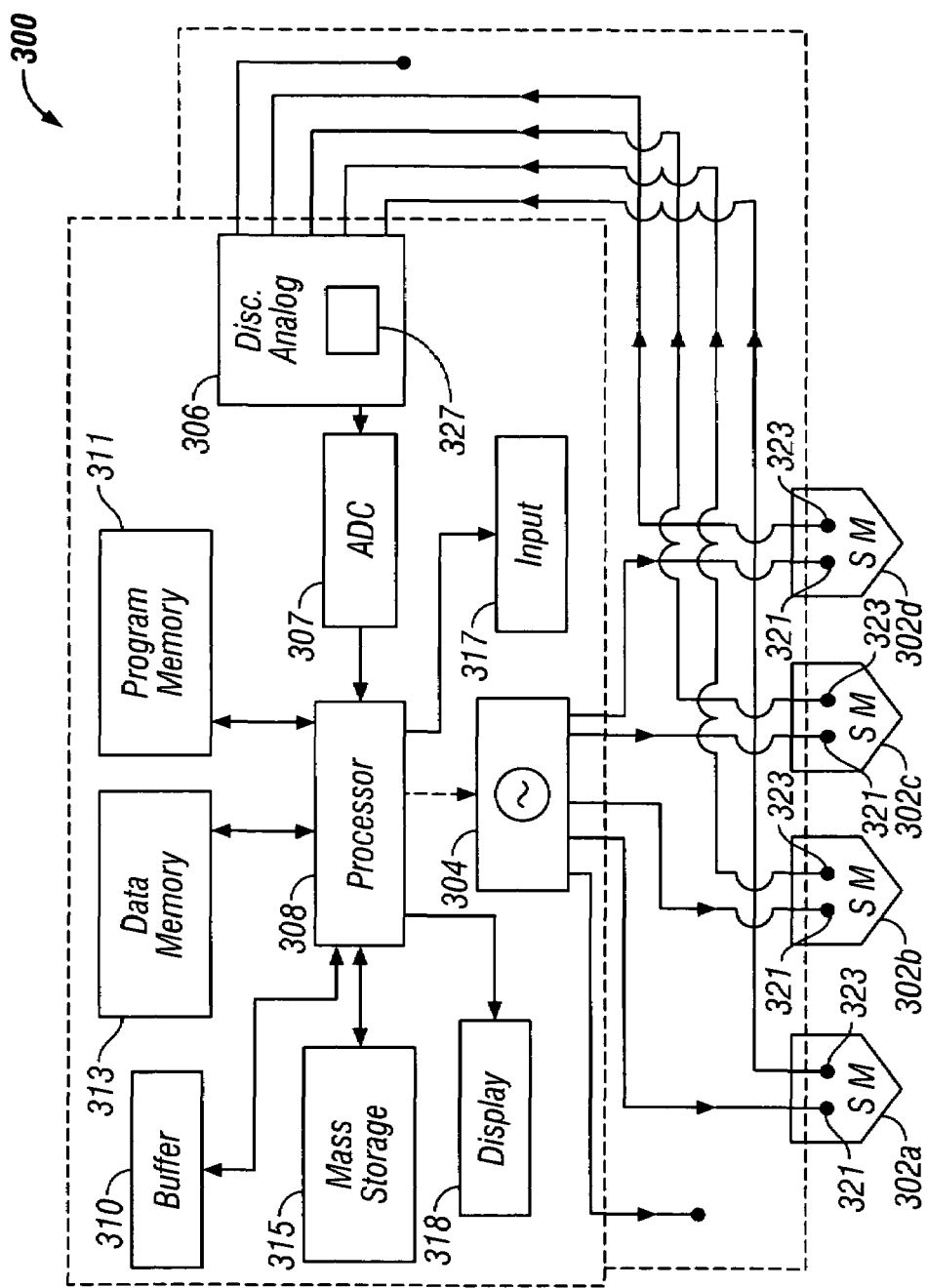
FIG. 3 is a block diagram of one exemplary embodiment of the apparatus for waveform assessment according to the invention.

Referring now to FIG. 3, an apparatus for identifying artifacts within the physiologic waveforms of a living subject (and using such information in the determination of cardiac output) is described. In the illustrated embodiment, the apparatus is adapted for the measurement of the cardiac output of a human being based on artifacts in the ECG waveform of the subject, although it will be recognized that other hemodynamic parameters and types of living organism may be evaluated in conjunction with the invention in its broadest sense.

The apparatus 300 of FIG. 3 fundamentally comprises a plurality of electrically conductive electrodes 302 (with individual terminals 321, 323) for supplying a current and measuring voltage (and impedance) from the subject non-invasively; a current source 304 coupled to at least a portion of the electrodes 302 for providing the alternating (AC) electrical current supplied to the subject; discrete analog circuitry 306 for preconditioning the analog impedance and ECG waveforms derived from the electrodes 302, an analog-to-digital converter (ADC) 307 for converting the conditioned analog signals to a binary digital format; a digital processor 308 operatively connected to the ADC 307 for analyzing the digital representations of the conditioned ECG and impedance waveforms; a buffer memory 310 for storing conditioned data prior to fiducial point detection; program and data memories 311, 313, for storing program instructions and data, respectively; a mass storage device 315, an input device 317 for receiving operation command and data from the apparatus user, and a display device 318 for displaying information such as data and waveforms, as well as applications program interface, to the user.

The electrodes 302 of the embodiment of FIG. 3 comprise so-called "spot" electrodes of the type well known in the medical arts, although it will be recognized that other types of electrodes, including band electrodes may be substituted. As used herein, the term "spot" electrode includes both single- and multi-terminal electrodes adapted for use in a localized area of the subject's physiology. Exemplary configurations of the multi-terminal spot electrode especially useful with the invention herein are described in co-pending U.S. utility and design patent application Ser. Nos. 09/613,183 and 29/128,623 respectively, filed Jul. 10, 2000 and Aug. 28, 2000, respectively, both assigned to the Assignee hereof, both incorporated by reference herein in their entirety.

In operation, the apparatus 300 generates an effectively constant current (via the current source 304) which is applied to certain ones of the terminal(s) 321 of the electrodes 302. The applied current derived from the current source 304 is a 70 kHz sine wave of approximately 2.5 mA maximum RMS. The measured voltage associated with the aforementioned sine wave is on the order of 75 mV maximum RMS. These values are chosen to advantageously minimize electric shock hazard, although it will be appreciated that other frequencies, currents, or voltages may be substituted. The construction and operation of AC current sources is well known in the electronic arts, and accordingly is not described further herein.

The preprocessor 306 and associated signal processing apparatus is in electrical communication with other electrodes 302, from which potentials (voltages) are measured. In the selected frequency range of the AC signal (e.g., 70 kHz), the typical impedance associated with a human subject's skin is 2 to 10 times the value of the underlying thoracic impedance $Z_T(t)$. To aid in eliminating the contribution from skin and tissue impedance, the apparatus of the present invention uses at least two, and typically four electrode arrays 302a–d for measurement, as shown in FIG. 3. In a simple application, one electrode array 302a comprising a stimulation electrode terminal 321 and a measurement electrode terminal 323 is applied above the thorax of the subject, while a second electrode array 302b (similarly having a stimulation electrode terminal and measurement electrode terminal) is applied below the thorax. The AC current from the current source is supplied to the stimulation electrode terminals 321. Current flows from each stimulation electrode terminal 321 through each constant skin impedance, $Z_{sk1}$ or $Z_{sk4}$, each constant body tissue impedance, $Z_{b1}$ or $Z_{b1}$, and each constant skin impedance, $Z_{sk2}$ or $Z_{sk3}$, to each measurement electrode terminal 323. The voltages at the measurement electrode terminals 323 are measured and input to a differential amplifier circuit 327 within the preprocessor 306 to obtain the differential voltage, $V_T(t)$. The desired thoracic impedance, $Z_T(t)$, is then obtained using the relationship of Eqn. 13.

$$Z_T(t) = \frac{V_T(t)}{I_T(t)} \qquad \text{(Eqn. 13)}$$

As shown in FIG. 3, two sets of electrode arrays 302a–d may advantageously be used to monitor the impedance associated with the left and right portion of the thorax in the present invention. When eight electrode terminals (four arrays 302a–d each with two terminals 321, 323) are used in this manner, the four measurement arrays are also used to obtain an electrocardiogram (ECG). As previously discussed, the sensed ECG data is used, inter alia, as an input to the AV pacing spike detector (for identification of the AV spike for substitution as the Q point), to determine the subject's heart rate, to identify the QRS complex and Q and R points, and as an input to the fiducial point detection algorithm for the impedance waveform.

It is noted that the apparatus 300 described herein may be constructed in a variety of different physical configurations, using a variety of different components, and measuring a variety of different parameters. For example, some or even all of the foregoing components may be physically integrated (such as in an application specific integrated circuit incorporating a DSP core, memory, "front" end analog processing, and ADC in a single piece of silicon), and/or the functionality associated with multiple components performed by a single multi-function component (e.g., a processor adapted to perform calculations associated with the AV spike detection methods disclosed herein, as well as host functions such as video display, bus arbitration, etc.). Exemplary configurations comprise the modular or pod arrangements disclosed in co-pending and co-owned U.S. patent application Ser. No. 09/903,473 filed Jul. 10, 2001 and entitled "Apparatus and Method for Determining Cardiac Output in a Living Subject", which is incorporated herein by reference in its entirety. Another exemplary configuration comprises a PC-based device of the type well known in the art, having a host microprocessor as well as the aforementioned preprocessing and signal processing functionality in the form of a separate DSP in data communication therewith. In yet another embodiment, the apparatus comprises a mobile personal computing device (such as a personal digital assistant, or PDA), which is adapted to receive input data from the electrodes 302 and analyze the data to produce a corrected measurement of cardiac output. It will also be recognized that other portable devices, such as laptop computers, calculators, and personal organizers, may conceivably be configured to run the computer program(s) of the present invention. Such portable devices are readily adapted to the methods of the present invention, since as a result of the invention's advantageous use of comparatively simple wavelet transforms, the processing and storage capability needed to implement the algorithm is decreased. Furthermore, a variety of different methods of transmitting the input sensor (i.e., electrode) data to these devices may be used, including networked computers, or even wireless data links.

Furthermore, ECG waveforms and analyses, cardiac output, LVET, SV, or other measurements generated by the foregoing apparatus 300 may also optionally be stored in the storage device 315 for later retrieval, or output to an external device such as a printer, data storage unit, other peripheral component via a serial or parallel port if desired. Furthermore, the apparatus 300 may be networked to another computing device or database (not shown) whereby the data generated by the apparatus may be remotely analyzed or stored. Transmission of output data to such remote devices may be accomplished using a variety of well understood methods, such as by local area network (LAN), intranet, Internet, fiber-optic systems, or radio frequency or IR (wireless) devices.

It will be further recognized that while the apparatus 300 of the invention is described herein as a substantially discrete or "stand-alone" system, the invention may be adapted to act as a plug in card, module, or other complementary device (including any supporting software) for an existing ECG or patient monitoring system that utilizes electrodes. Hence, the invention can advantageously be "retro-fitted" to such prior art systems, thereby extending the utility of the pre-existing system, and potentially obviating the purchase of entirely new equipment.

Computer Program

A computer program for implementing the aforementioned methods of ECG waveform analysis is now described. In one exemplary embodiment, the computer program comprises an object ("machine") code representation of an assembly source code listing implementing the cardiographic spike detection and associated cardiac output (wavelet transform) methodologies previously described herein, either individually or in combination thereof. While assembly language is used for the present embodiment, it will be appreciated that other programming languages may be used, including for example VisualBasic™, Fortran, C, and $C^{++}$. The object code representation of the source code listing is compiled and disposed on a media storage device of the type well known in the computer arts. Such media storage devices can include, without limitation, optical discs, CD ROMs, DVDs, magnetic floppy disks or "hard" drives, tape drives, or even magnetic bubble memory. The computer program further comprises a graphical user interface (GUI) of the type well known in the programming arts, which is operatively coupled to the display and input device of the host computer or apparatus 300 on which the program is run.

In terms of general structure, the program is in one embodiment comprised of a series of subroutines or algorithms for implementing the methodologies described herein based on measured parametric data (e.g., the "input parameters" previously defined) which are provided to the host computer. In a second embodiment, the computer program comprises an assembly language/micro-coded instruction set disposed within the embedded storage device, i.e. program memory, of a digital signal processor (DSP) or microprocessor associated with the foregoing hemodynamic measurement apparatus of FIG. 3.

Method of Providing Treatment

Figure 4:
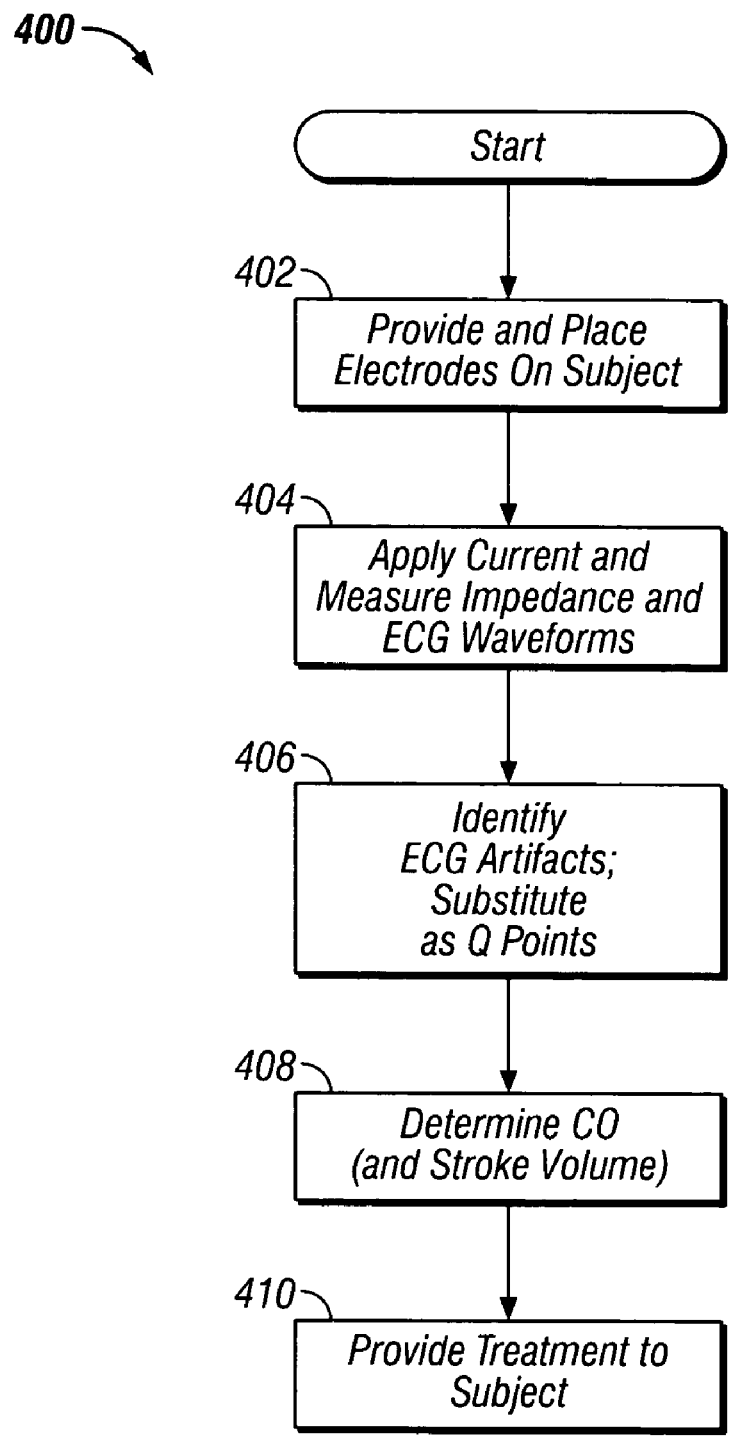
FIG. 4 is a logical flow diagram illustrating one exemplary embodiment of the method of providing treatment to a subject using the aforementioned methods.

Referring now to FIG. 4, a method of providing treatment to a subject using the aforementioned methods of artifact detection is described. While the following discussion is cast in terms of the aforementioned methods and algorithms adapted for identifying AV spikes in ECG waveforms (and determination of cardiac output based thereon), it will be recognized that the method or providing treatment described herein is more broadly applicable to treatment based on the assessment of any hemodynamic property or parameter based on artifact detection.

As shown in FIG. 4, the method of providing treatment 400 generally comprises first disposing a plurality of impedance cardiography electrodes with respect to the thoracic cavity of the subject per step 402. As previously discussed, the electrodes 302 of the exemplary configuration comprise the multi-terminal type described above with respect to FIG. 3 (or other suitable configuration), and are disposed above and below the thorax of the subject such that at least one stimulation terminal and one excitation terminal are above and below the thorax. Next, the impedance waveform (and ECG) data of the subject are measured non-invasively via the electrodes 302 per step 404; specifically for example by applying a constant AC waveform to the stimulation terminal(s), and measuring the resultant voltage at the measurement terminal(s).

In step 406, the ECG data is analyzed to identify artifacts therein. Specifically, in the instant embodiment, the aforementioned filtering, golden section search, and fuzzy algorithms are used to identify the AV pacing spikes within the data, and use this information as substitute Q points for further evaluation of the impedance waveform using, e.g., discrete wavelet transforms as previously discussed herein. Stroke volume and cardiac output (CO) of the subject are next determined in step 408 based on the fiducial points determined in step 406, and the heart rate (HR) derived from the subject from the ECG waveform as needed.

Lastly, a course of treatment is determined and provided to the subject per step 410 based on the cardiac output (CO) of step 408. Such course of treatment may include, for example, the intravenous injection of pharmacological agents, angioplasty, or other such measures aimed at increasing cardiac output or otherwise stemming further degradation of the subject's cardiac function.

It will be recognized that while certain aspects of the invention have been described in terms of a specific sequence of steps of a method, these descriptions are only illustrative of the broader methods of the invention, and may be modified as required by the particular application. Certain steps may be rendered unnecessary or optional under certain circumstances. Additionally, certain steps or functionality may be added to the disclosed embodiments, or the order of performance of two or more steps permuted. All such variations are considered to be encompassed within the invention disclosed and claimed herein.

While the above detailed description has shown, described, and pointed out novel features of the invention as applied to various embodiments, it will be understood that various omissions, substitutions, and changes in the form and details of the device or process illustrated may be made by those skilled in the art without departing from the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. A method of identifying an artifact in a cardiographic waveform, comprising:
   providing at least one cardiographic waveform;
   determining the shape of at least one of said artifacts within said waveform using an iterative interval search; and
   identifying said artifact based at least in part on said shape;
   wherein said act of identifying further comprises analyzing said shape with respect to a variable noise threshold.

2. A method of identifying an artifact in a cardiographic waveform, comprising:
   providing at least one cardiographic waveform;
   determining the shape said artifacts within said waveform; and
   identifying said artifact based at least in part on said shape;
   wherein said act of identifying further comprises analyzing the noise threshold associated with said at least one waveform using fuzzy logic.

3. A method of identifying at least one artifact within a waveform, comprising:
   sampling said waveform at a first frequency to produce sampled data;
   filtering said sampled data according to a first pass band to produce first filtered data;
   filtering said first filtered data according to a second pass band to produce second filtered data;
   determining at least one noise threshold based at least in part on said second filtered data; and
   identifying at least one artifact from said waveform based at least in part on said at least one noise threshold.

4. The method of claim 3, wherein said act of identifying at least one artifact comprises performing at least one golden section search.

5. The method of claim 3, wherein said act of determining at least one noise threshold comprises analyzing at least a portion of said second filtered using fuzzy logic.

6. A method of processing waveform data, comprising:
   sampling said waveform at a first frequency to produce sampled data;
   filtering said sampled data according to at least one filter scheme to produce filtered data; and
   determining at least one noise threshold associated with said waveform based at least in part on fuzzy logic analysis of said filtered data.

7. The method of claim 6, wherein said act of filtering comprises:
   high pass filtering said sampled data according to a first pass band; and
   low pass filtering said high pass filtered data according to a second pass band.

8. The method of claim 6, wherein said act of determining at least one noise threshold comprises:
   fuzzification of at least a portion of said filtered data to produce a plurality of fuzzy inputs;
   mapping at least a portion of said fuzzy inputs to a plurality of fuzzy outputs; and
   determining said at least one noise threshold based at least on part on said plurality of fuzzy outputs.

9. The method of claim 8, wherein said act of fuzzification comprises generating said plurality of fuzzy inputs based on at least one membership function and said at least portion of filtered data.

10. The method of claim 8, wherein said act of mapping comprises mapping using a rule based inference (RBI) process.

11. The method of 8, wherein said act of determining said at least one noise threshold comprises:
    providing at least one output membership function; and
    defuzzification of said plurality of fuzzy outputs into at least one crisp noise threshold value.

12. Apparatus adapted for analysis of physiologic data, comprising:
    at least one data input, said at least one input adapted for operative coupling to at least one device adapted to produce signals derived from a living subject;
    a data processor operatively coupled to receive data from said at least one input; and
    a computer program adapted to run on said at least one processor, said computer program further comprising:
    a filtering algorithm;
    a noise threshold algorithm; and
    an artifact detector algorithm.

13. The apparatus of claim 12, wherein said computer program further comprises:
    a delay adapter algorithm, and
    an artifact discriminator algorithm.

14. The apparatus of claim 12, wherein said computer program further comprises a pace algorithm adapted for associating at least one detected artifact within a waveform with another event within said waveform.

15. The apparatus of claim 12, wherein said noise threshold algorithm comprises at least one fuzzy logic analysis algorithm.

16. The apparatus of claim 15, wherein said artifact detector algorithm comprises at least one golden section search algorithm.

17. The apparatus of claim 12, wherein said artifact detector algorithm comprises at least one golden section search algorithm.

18. The apparatus of claim 12, wherein said at least one device adapted to produce signals comprises a plurality of electrodes, each of said electrodes having a plurality of terminals spaced at a predetermined distance.

19. The apparatus of claim 12, wherein said apparatus comprises an impedance cardiography (ICG) device, and said data comprises both ECG and impedance data.

20. Apparatus adapted to identify an artifact in physiologic waveforms from a living subject, comprising:
a digital processor adapted to run algorithms thereon;
at least one electrode in operative communication with said processor and adapted to provide at least one physiologic waveform from said subject;
a fuzzy logic algorithm adapted to identify at least one noise threshold within said at least one physiologic waveform; and
an iterative interval search algorithm adapted to identify said artifact based at least in part on said noise threshold and said waveform.

21. A method of dynamically adjusting the delay associated with a plurality of waveform artifacts, comprising:
providing a first delay value;
evaluating said first delay value with respect to at least two of said waveform artifacts during a first iteration; and
adjusting said first delay value to a second delay value during a second iteration based at least in part on said act of evaluating.

22. The method of claim 21, wherein said act of evaluating comprises determining the number of occurrences of said artifacts with a pre-selected sampling interval.

23. The method of claim 22, wherein said method comprises dynamically adjusting the delay associated with the atrial and ventricular spikes associated with an ECG waveform.

24. A method of discriminating between a plurality of artifacts in a waveform, comprising:
identifying a plurality of artifacts;
classifying individual ones of said artifacts according to a first classification having at least two types; and
evaluating said artifacts based on said first classification by:
if one or more artifacts of only one of said types is present, assigning at least one of said artifacts of said one type as an artifact of interest; or
if at least one artifact of each of said at least two types are present, assigning an artifact of a preselected one of said at least two types as an artifact of interest.

25. The method of claim 24, wherein said act of classifying according to at least two types comprises classifying said artifacts as either atrial or ventricular spikes.

26. The method of claim 24, wherein said act of assigning an artifact of a preselected type comprises assigning a ventricular spike as the Q point in an ECG waveform.

27. A method of discriminating between a plurality of artifacts in an electrocardiographic waveform, comprising:
identifying a plurality of artifacts;
classifying, using at least a computer program, individual ones of said artifacts according to a first classification having multiple types; and
evaluating, using at least a computer program, said artifacts based on said first classification by:
if one or more artifacts of only one of said multiple types is present, assigning at least one of said artifacts of said one type as an artifact of interest; or
if at least one artifact of each of said multiple types are present, assigning at least one artifact of a preselected one of said multiple types as an artifact of interest.

28. Apparatus adapted to identify an artifact in physiologic waveforms from a living subject, comprising:
digital processor means for running algorithms thereon;
at least one sensor means, in operative communication with said processor means, for providing at least one physiologic waveform from said subject;
fuzzy logic algorithm means adapted to identify at least one noise threshold within said at least one physiologic waveform; and
iterative interval search algorithm means adapted to identify said artifact based at least in part on said noise threshold and said waveform.

29. A method of detecting an artifact in a waveform, said artifact having at least one feature, comprising:
providing at least one waveform;
determining at least one noise threshold with respect to said at least one waveform; and
detecting said artifact based at least in part on said at least one noise threshold and said at least one feature, said detecting comprising performing at least one iterative interval search.

30. The method of claim 29, wherein said act of performing at least one iterative interval search comprises identifying the shape of said artifact using said search.

31. The method of claim 30, wherein said at least one iterative interval search comprises iteratively evaluating a search interval using a golden section search, and said act of identifying the shape comprises identifying at least two points at which function values are compared, said at least two points being symmetrically located in said search interval during each of said search iterations.

32. The method of claim 30, further comprising specifying at least one uncertainty interval.

33. The method of claim 32, further comprising reducing the length of said at least one uncertainty interval by given value.

34. The method of claim 33, wherein said given value comprises a fixed ratio.

35. A method of detecting an artifact in a ECG waveform based on shape, comprising:
providing at least one ECG waveform;
determining a noise threshold value using at least one fuzzy variable; and
detecting said artifact based at least in part on said shape and said at least one noise parameter.

36. A method of detecting an artifact in a physiologic waveform based on shape, comprising:
providing at least one physiologic waveform;
determining at least one noise parameter with respect to said at least one waveform; and
detecting said artifact based at least in part on said shape and said at least one noise parameter, said act of detecting comprising performing at least iterative interval search.

37. Apparatus adapted to identify an artifact in physiologic waveforms from a living subject, comprising:
a digital processor adapted to run computer programs thereon;
at least one electrode in operative communication with said processor and adapted to provide at least one physiologic waveform from said subject; and
a computer program adapted to:
determine the shape of said artifact within said at least one waveform; and
identify said artifact based at least in part on said shape; and selectively substitute said artifact for at least one fiducial point within said at least one waveform.

38. The apparatus of claim 37, wherein said computer program is further adapted to determine a noise threshold associated with said at least one waveform.

39. The apparatus of claim 37, wherein said at least one fiducial point comprises the Q point within an ECG waveform.

40. The apparatus of claim 39, wherein said computer program is further adapted to utilize said substituted artifact in the definition of a search interval used with another waveform.

41. A method of detecting an artifact in a waveform, said artifact having at least one feature, comprising:
   a step for providing at least one waveform;
   a step for determining at least one noise threshold with respect to said at least one waveform; and
   a step for detecting said artifact based at least in part on said at least one noise threshold and said at least one feature, said set for detecting further comprising performing at least one iterative interval search including at least identifying the shape of said artifact using said search, said at least one iterative interval search comprising iteratively evaluating a search interval using a golden section search, said act of identifying the shape comprising identifying at least two points at which function values are compared, said at least two points being symmetrically located in said search interval during each of a plurality of search iterations;
   wherein said step for providing at least one waveform comprises a step for providing an ECG, and said step for detecting an artifact comprises a step for detecting a feature related to the coronary function of a living subject.

42. An apparatus for discriminating between a plurality of artifacts in an electrocardiographic waveform, comprising:
   means for identifying a plurality of artifacts;
   means for classifying, using at least a computer program, individual ones of said artifacts according to a first classification having multiple types; and
   means for evaluating, using at least a computer program, said artifacts based on said first classification by:
      if one or more artifacts of only one of said multiple types is present, assigning at least one of said artifacts of said one type as an artifact of interest; or
      if at least one artifact of each of said multiple types are present, assigning at least one artifact of a preselected one of said multiple types as an artifact of interest.

43. An apparatus for detecting an artifact in a waveform, said artifact having at least one feature, comprising:
   means for providing at least one waveform;
   means for determining at least one noise threshold with respect to said at least one waveform; and
   means for detecting said artifact based at least in part on said at least one noise threshold and said at least one feature, said means for detecting being adapted to perform at least one iterative interval search.

44. The apparatus of claim 43, wherein said means for performing at least one iterative interval search comprises:
   means for identifying the shape of said artifact based at least in part on said search.

45. The apparatus of claim 44, wherein said means for performing at least one iterative interval search comprises:
   means for iteratively evaluating a search interval using a golden section search, and said act of identifying the shape comprises identifying at least two points at which function values are compared, said at least two points being symmetrically located in said search interval during each of said search iterations.

46. The apparatus of claim 45, further comprising specifying at least one uncertainty interval.

47. The apparatus of claim 46, further comprising reducing the length of said at least one uncertainty interval by given value.

48. The apparatus of claim 47, wherein said given value comprises a fixed ratio.

* * * * *